United States Patent
Larson (10) Patent No.: US 8,968,313 B2
(45) Date of Patent: Mar. 3, 2015

(54) ELECTROSURGICAL INSTRUMENT WITH A KNIFE BLADE STOP

(71) Applicant: Covidien LP, Mansfield, MA (US)

(72) Inventor: Eric R. Larson, Boulder, CO (US)

(73) Assignee: Covidien LP, Mansfield, MA (US)

(*) Notice: Subject to any disclaimer, the term of this patent is extended or adjusted under 35 U.S.C. 154(b) by 87 days.

(21) Appl. No.: 13/799,173

(22) Filed: Mar. 13, 2013

(65) Prior Publication Data

US 2013/0331837 A1    Dec. 12, 2013

Related U.S. Application Data

(60) Provisional application No. 61/658,555, filed on Jun. 12, 2012.

(51) Int. Cl.
*A61B 18/18* (2006.01)
*A61B 18/14* (2006.01)
*A61B 19/00* (2006.01)

(52) U.S. Cl.
CPC ......... *A61B 18/1447* (2013.01); *A61B 18/1445* (2013.01); *A61B 2018/1455* (2013.01); *A61B 2019/304* (2013.01)
USPC .......................................................... 606/51

(58) Field of Classification Search
USPC .................................... 606/32–52
See application file for complete search history.

(56) References Cited

U.S. PATENT DOCUMENTS

| D249,549 S | 9/1978 | Pike |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |

(Continued)

FOREIGN PATENT DOCUMENTS

| CN | 201299462 | 9/2009 |
|---|---|---|
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Scott Getzow (57) ABSTRACT

An electrosurgical forceps is provided with a shaft that extends from a housing of the electrosurgical forceps. An end effector assembly operably coupled to a distal end of the shaft includes a pair of first and second jaw members one of which being movable from an open configuration for positioning tissue therebetween, to a clamping configuration for grasping tissue therebetween. A knife blade assembly includes a knife blade that is translatable within the first and second jaw members when the first and second jaw members are in the clamping configuration. The knife blade assembly includes a medial portion defining an opening therethrough having proximal and distal ends. A knife blade stop in operative communication with the knife blade assembly includes a pair of leading and trailing stops thereon that are configured to contact respective distal and proximal ends of the opening to limit translation of the knife blade assembly.

14 Claims, 5 Drawing Sheets

(56) References Cited

U.S. PATENT DOCUMENTS

| | | | |
|---|---|---|---|
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| 2007/0260242 A1* | 11/2007 | Dycus et al. ............ 606/51 |
| 2010/0256634 A1* | 10/2010 | Voegele et al. ............ 606/45 |
| 2013/0150842 A1 | 6/2013 | Nau, Jr. |
| 2013/0178852 A1 | 7/2013 | Allen, IV |

FOREIGN PATENT DOCUMENTS

| | | |
|---|---|---|
| DE | 2514501 | 10/1976 |
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10031773 | 11/2001 |
| DE | 19946527 | 12/2001 |
| DE | 20121161 | 4/2002 |
| DE | 10045375 | 10/2002 |
| DE | 10 2004 026179 | 12/2005 |
| DE | 20 2007 009318 | 8/2007 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-000538 | 1/1997 |
| JP | 9-10223 | 1/1997 |
| JP | 9-122138 | 5/1997 |
| JP | 10-000195 | 1/1998 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2002-136525 | 5/2002 |
| JP | 2003-116871 | 4/2003 |
| JP | 2003-175052 | 6/2003 |
| JP | 2003-245285 | 9/2003 |
| JP | 2004-517668 | 6/2004 |
| JP | 2004-528869 | 9/2004 |
| JP | 2005-152663 | 6/2005 |
| JP | 2005-253789 | 9/2005 |
| JP | 2006-015078 | 1/2006 |
| JP | 2006-501939 | 1/2006 |
| JP | 2006-095316 | 4/2006 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 02/45589 | 6/2002 |
| WO | WO 2005/110264 | 11/2005 |
| WO | WO 2006/021269 | 3/2006 |
| WO | WO 2008/040483 | 4/2008 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.

(56) References Cited

OTHER PUBLICATIONS

U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 9, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/741,550, filed Jan. 15, 2013, Deborski.
U.S. Appl. No. 13/731,674, filed Dec. 31, 2012, Siebrecht.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/853,259, filed Mar. 29, 2013, Garrison.
U.S. Appl. No. 13/853,273, filed Mar. 29, 2013, Kerr.
U.S. Appl. No. 13/853,339, filed Mar. 29, 2013, Reschke.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.

(56) References Cited

OTHER PUBLICATIONS

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

\* cited by examiner

ELECTROSURGICAL INSTRUMENT WITH A KNIFE BLADE STOP

CROSS REFERENCE TO RELATED APPLICATION

The present application claims the benefit of and priority to U.S. Provisional Application Ser. No. 61/658,555, filed on Jun. 12, 2012, the entire contents of which are incorporated herein by reference.

BACKGROUND

1. Technical Field

The present disclosure relates to an electrosurgical instrument and, more particularly, to an electrosurgical instrument including a knife blade stop configured to limit proximal and distal movement of a knife blade of the electrosurgical instrument.

2. Description of Related Art

Electrosurgical forceps are well known in the medical arts. For example, an electrosurgical endoscopic forceps is utilized in surgical procedures, e.g., laparoscopic surgical procedure, where access to tissue is accomplished through a cannula or other suitable device positioned in an opening on a patient. The endoscopic forceps, typically, includes a housing, a handle assembly including a movable handle, a drive assembly, a shaft, a cutting mechanism such as, for example, a knife blade assembly, and an end effector assembly attached to a distal end of the shaft. The end effector includes jaw members that operably communicate with the drive assembly to manipulate tissue, e.g., grasp and seal tissue. Typically, the endoscopic forceps utilizes both mechanical clamping action and electrical energy to effect hemostasis by heating the tissue and blood vessels to coagulate, cauterize, seal, cut, desiccate, and/or fulgurate tissue. Typically, subsequent to effecting hemostasis, a knife blade of the knife blade assembly is deployed to sever the effected tissue.

Conventional endoscopic forceps, typically, utilize one or more components associated with the endoscopic forceps to limit proximal and/or distal movement of the knife blade assembly. For example, one or more of the jaw members, shaft, cam or pivot pins, which are, typically, hard surfaces, are sometimes configured to contact the knife blade assembly (or operable component associated therewith) to limit movement of the knife blade assembly in either of the proximal or distal directions. Repeated contact between the knife blade assembly and one or more of the aforementioned components may cause the knife blade assembly to develop what is commonly referred to in the art as "fatigue cracking."

SUMMARY

In view of the foregoing, it may prove useful in the medical arts to provide a knife blade stop configured limit proximal and distal movement of a knife blade of the electrosurgical instrument.

Aspects of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides an electrosurgical forceps with a shaft that extends from a housing of the electrosurgical forceps. An end effector assembly operably coupled to a distal end of the shaft includes a pair of first and second jaw members one of which being movable from an open configuration for positioning tissue therebetween, to a clamping configuration for grasping tissue therebetween. A knife blade assembly includes a knife blade that is translatable within the first and second jaw members when the first and second jaw members are in the clamping configuration. The knife blade assembly includes a medial portion defining an opening therethrough having proximal and distal ends. A knife blade stop in operative communication with the knife blade assembly includes a pair of leading and trailing stops thereon that are configured to contact respective distal and proximal ends of the opening to limit translation of the knife blade assembly.

The knife blade stop may be operably disposed on the knife blade assembly and the knife blade assembly may be movable through leading and trailing openings on the knife blade stop.

In certain instances, the knife blade stop includes an aperture that is configured to receive a pivot pin therethrough. In this instance, the pivot pin provides a pivot for the first and second jaw members.

In certain instances, the knife blade stop includes an elongated slot that is configured to receive a cam pin therethrough. In this instance, the cam pin is configured to move the first and second jaw members between the open and clamping configurations.

In certain instances, knife blade stop may also include an elongated groove thereon that is configured to receive at least one wire that is configured to provide electrosurgical energy to the first and second jaw members.

The knife blade stop may be made from two portions of relatively soft injection molded plastic joined together in a mechanical manner.

An aspect of the present disclosure provides an electrosurgical forceps with a shaft that extends from a housing of the electrosurgical forceps. An end effector assembly operably coupled to a distal end of the shaft includes a pair of first and second jaw members one of which being movable from an open configuration for positioning tissue therebetween, to a clamping configuration for grasping tissue therebetween. A knife blade assembly includes a knife blade that is translatable within the first and second jaw members when the first and second jaw members are in the clamping configuration. The knife blade assembly includes a bifurcated medial portion defining an opening therethrough having proximal and distal ends. A knife blade stop configured to receive the knife blade assembly therethrough includes a pair of leading and trailing stops thereon that are positionable within the opening defined by the bifurcated medial portion. The leading and trailing stops are configured to contact respective distal and proximal ends of the opening to limit translation of the knife blade assembly. The knife blade stop includes an aperture that is configured to receive a pivot pin therethrough. The pivot pin provides a pivot for the first and second jaw members. The knife blade stop includes an elongated slot that is configured to receive a cam pin therethrough. The cam pin is configured to move the first and second jaw members between the open and clamping configurations. The knife blade stop may also include an elongated groove thereon that is configured to receive at least one wire that is configured to provide electrosurgical energy to the first and second jaw members.

The knife blade stop may be operably disposed on the knife blade assembly and the knife blade assembly may be movable through leading and trailing openings on the knife blade stop.

The knife blade stop may be made from two portions of relatively soft injection molded plastic joined together in a mechanical manner.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
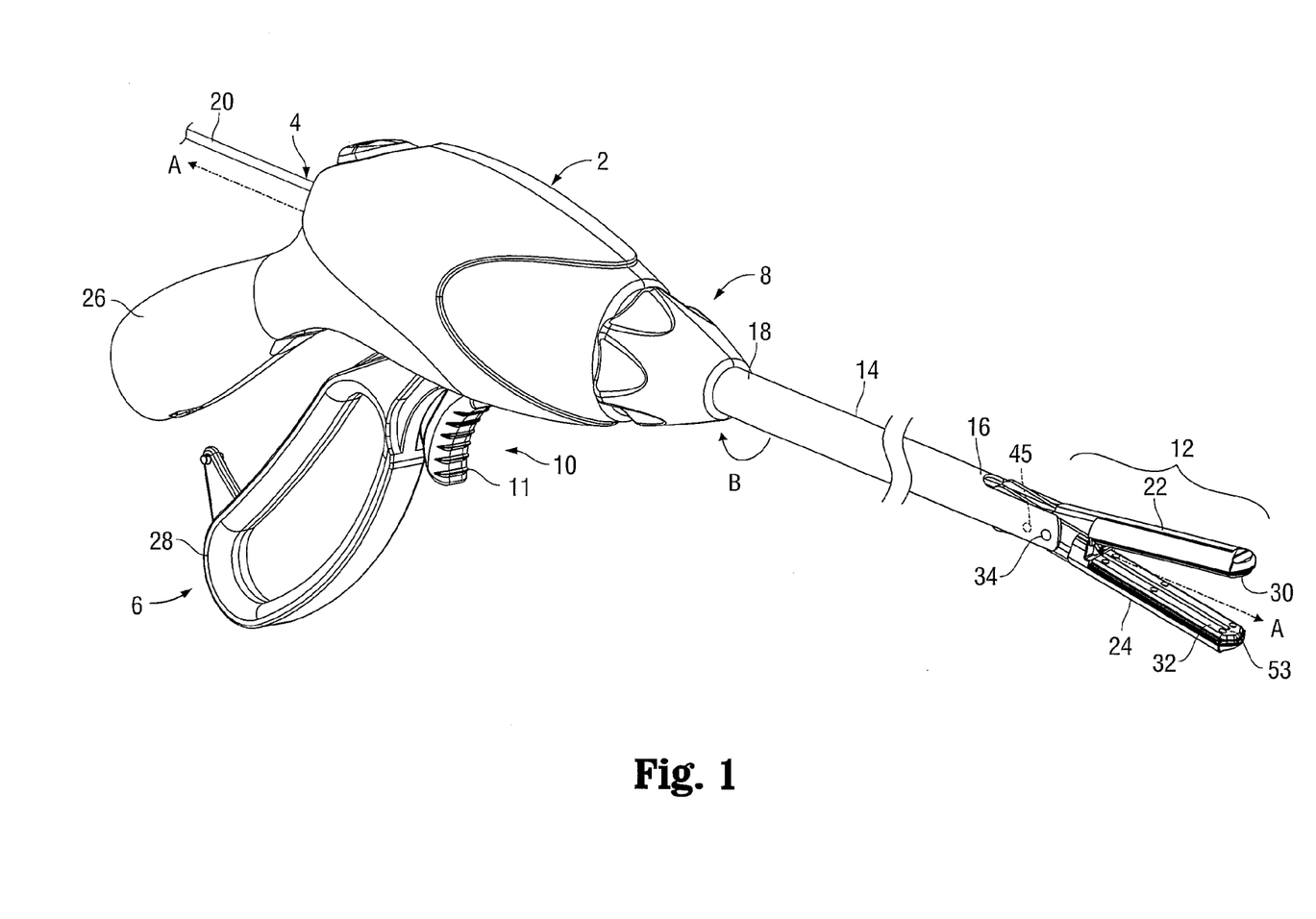
FIG. 1 is a perspective view of an endoscopic electrosurgical forceps according to an embodiment of the present disclosure.

Turning now to FIG. 1, an electrosurgical endoscopic forceps 2 (forceps 2) configured for use with a knife blade stop 40 (blade stop 40, see FIGS. 2-5) is illustrated. Forceps 2 includes a housing 4, a handle assembly 6, a rotating assembly 8, a trigger assembly 10 and an end effector assembly 12. Forceps 2 further includes a shaft 14 extending from the housing and having a longitudinal axis "A-A" defined therethrough. A distal end 16 of the shaft 14 is configured to mechanically engage end effector assembly 12 and a proximal end 18 is configured to mechanically engage housing 4. Forceps 2 also includes electrosurgical cable 20 that connects forceps 2 to a generator (not shown) or other suitable power source. Forceps 2 may alternatively be configured as a battery-powered instrument. Cable 20 includes a wire (or wires) (not explicitly shown) extending therethrough that has sufficient length to extend through shaft 14 in order to provide one or more suitable types of energy to one or both of a pair of jaw members 22 and 24 of end effector assembly 12. The generator may be configured to provide electrosurgical energy (e.g., RF, microwave, etc.,), thermal energy, ultrasonic energy, and the like to the pair of jaw members 22 and 24. In the illustrated embodiment, the generator is configured to provide RF energy to the jaw members 22 and 24.

While the blade stop 40 is described in terms of use with an endoscopic forceps, it is within the purview of the present disclosure that the blade stop 40 may be configured for use with an open forceps. In this instance, the blade stop 40 may be configured to accommodate the specific design of the open forceps.

Rotating assembly 8 is rotatable in either direction about longitudinal axis "A-A" to rotate end effector 12 about longitudinal axis "A-A," FIG. 1. Housing 4 houses the internal working components of forceps 2, such as a drive assembly (not explicitly shown), working components of the handle assembly 6, electrical raceways associated with the cable 20, and other working components therein.

Figure 2:
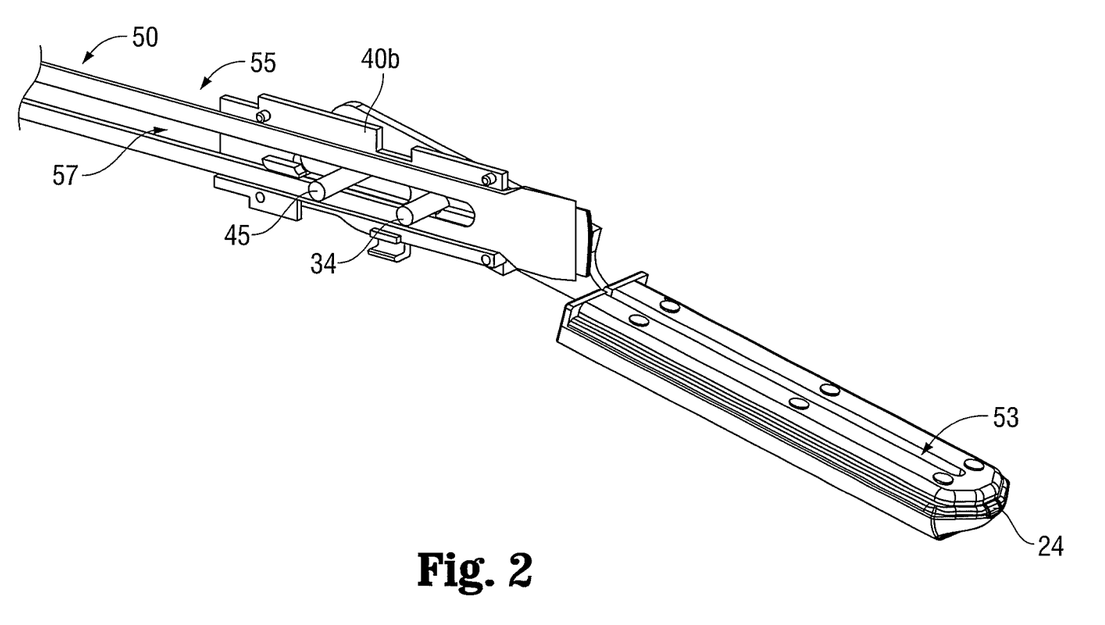
FIG. 2 is a partial, perspective view of the endoscopic electrosurgical forceps with a shaft and one of a pair of jaw members removed to illustrate a knife blade stop coupled to a knife blade assembly configured for use with the endoscopic forceps depicted in FIG. 1.
Figure 3:
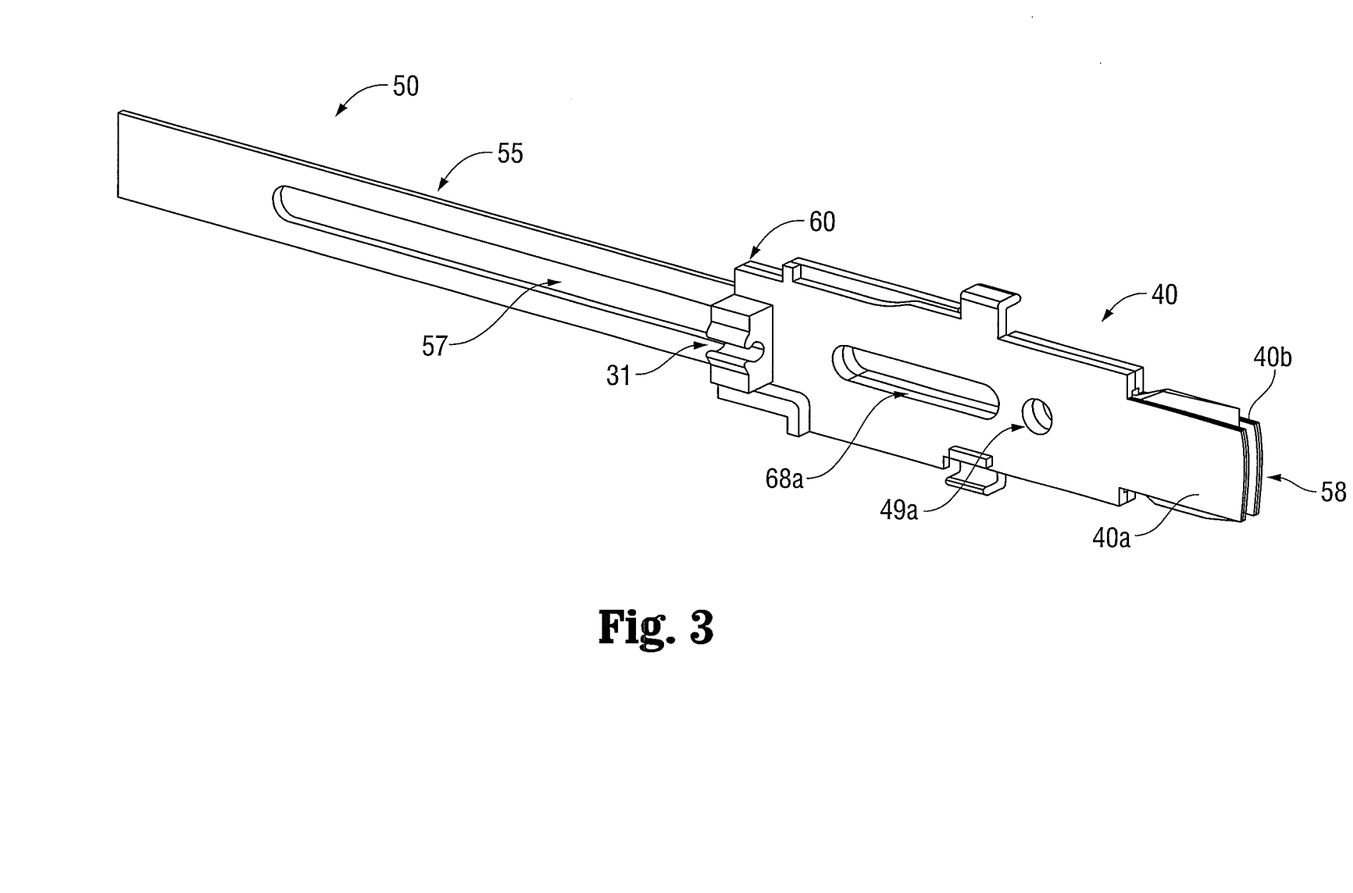
FIG. 3 is a partial, perspective view of the knife blade assembly and knife blade stop coupled to one another.

With continued reference to FIG. 1, handle assembly 6 includes a fixed handle 26 and a moveable handle 28. Fixed handle 26 is integrally associated with housing 4 and movable handle 28 is moveable relative to fixed handle 26. Moveable handle 28 of handle assembly 6 is ultimately connected to the drive assembly such that, together, movable handle 28 and drive assembly mechanically cooperate to impart movement of jaw members 22 and 24 between a spaced-apart position and an approximated position to grasp tissue disposed between treatment surfaces 30 and 32 of jaw members 22, 24, respectively. As shown in FIG. 1, moveable handle 28 is initially spaced-apart from fixed handle 26 and, correspondingly, jaw members 22, 24 are in the spaced-apart position (FIGS. 1-3). Moveable handle 28 is depressible from this initial position (FIG. 1) to a depressed position (not explicitly shown) corresponding to the approximated position of jaw members 22, 24.

Other methods for opening and closing the jaw members 22, 24 may be utilized. For example, any number of linkage devices, gears, vacuum tubes, actuators and the like may be utilized alone or in combination with the movable handle 24 and/or drive rod to impart movement of the jaw members 22, 24 from the spaced-apart position to the approximated position.

With reference to FIG. 2, a partial, perspective view of the forceps 2 with shaft 14 and jaw member 22 removed is provided to illustrate blade stop 40 coupled to a knife blade assembly 50 that is configured for use with the forceps 2. Blade stop 40 may be made from any suitable material. In accordance with the instant disclosure, blade stop 40 is made from a relatively soft plastic that provides little or no give when contacted by the knife blade assembly 50. Blade stop 40 may be formed and/or assembled via any suitable forming methods. For example, and in one particular embodiment, blade stop 40 is formed from two individually molded portions 40a and 40b that are configured to engage one another via one or more suitable engagement methods (FIGS. 2-5).

In the illustrated embodiment, portion 40b includes a top pair of detents 41 and a bottom pair of indents 43 (FIG. 4) that are each configured to engage a corresponding pair of indents and detents (not explicitly shown) disposed on the portion 40a. As can be appreciated, this indent/detent configuration can be altered, changed and/or modified as needed. In certain embodiments, the blade stop 40 may be cast as a unitary member, e.g., blade stop 40 may be monolithically formed.

Figure 4:
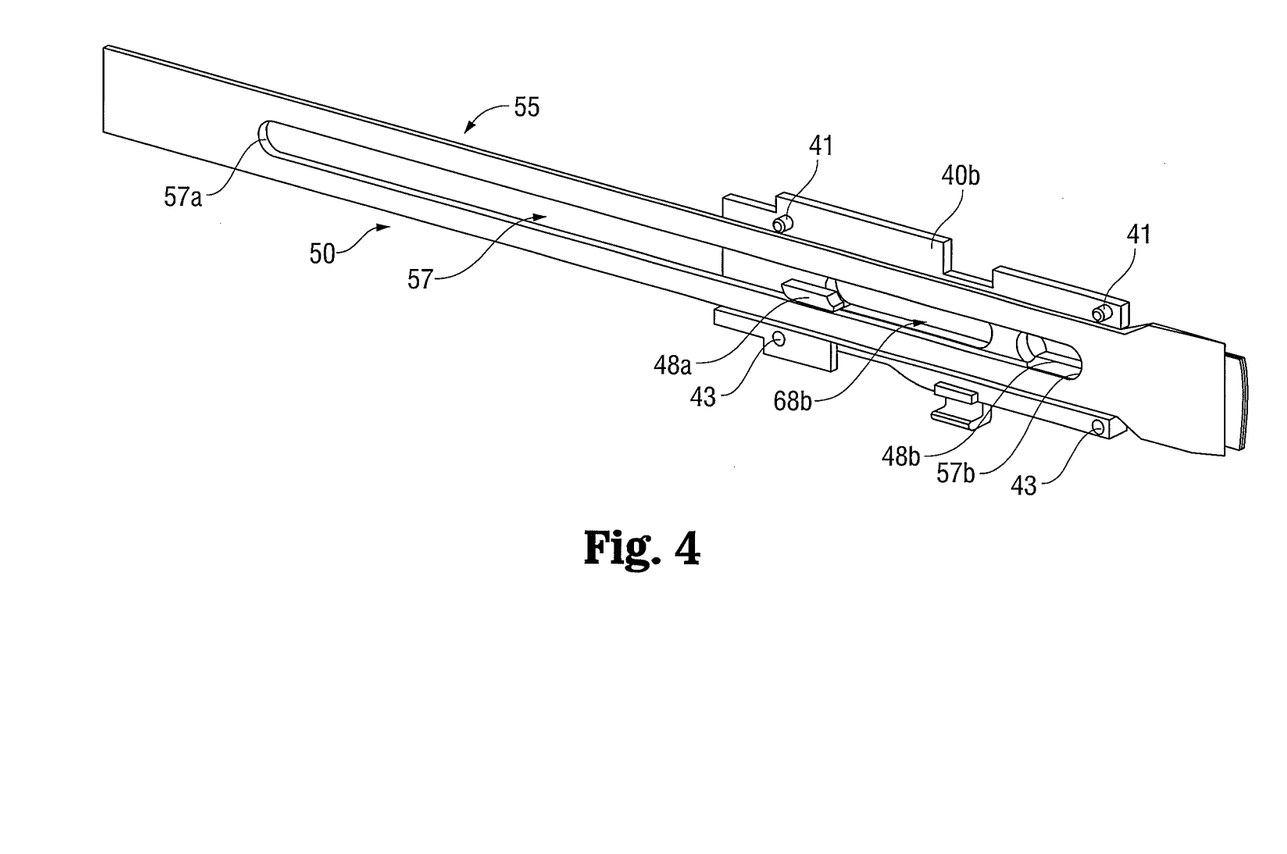
FIG. 4 is a partial, perspective view of the knife blade assembly and knife blade stop coupled to one another with a portion of the knife blade stop removed.
Figure 5:
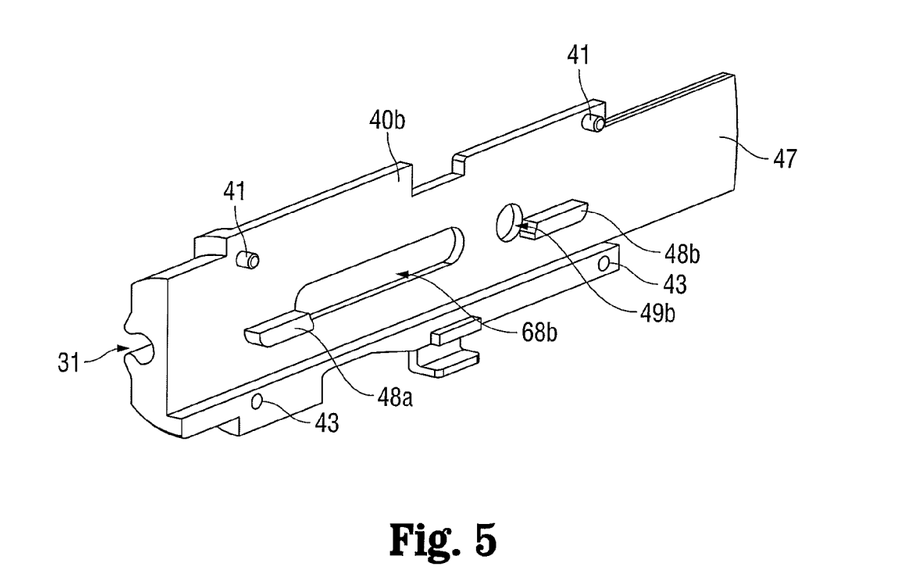
FIG. 5 is a partial, perspective view of the knife blade stop.

Blade stop 40 is in operative communication with the knife blade assembly 50 and includes a generally rectangular configuration that complements the shape of the knife blade assembly 50 (see FIGS. 2-4 for example). In an assembled configuration, blade stop 40 includes open leading and trailing openings 58 and 60 (as best seen in FIG. 3), respectively, that are configured to allow the knife assembly 50 to translate therethrough from a retracted configuration (FIGS. 2-4) to an extended configuration (not explicitly shown).

A pair of trailing and leading stops 48a and 48b (best seen in FIG. 5) is disposed on an interior of one (or in certain instances both) of the portions 40a and 40b. For illustrative purposes, trailing and leading stops 48a, 48b are shown on the portion 40b. Leading stop 48b is configured as a retraction stop and trailing stop 48a is configured as a deployment stop. In particular, leading stop 48b is configured to engage a distal end 57b of an opening 57 of the knife assembly 50 to limit proximal translation of the knife assembly 50 (as best seen in FIGS. 2 and 4). Likewise, trailing stop 48a is configured to engage a proximal end 57a (FIGS. 3 and 4) of opening 57 to limit distal translation of the knife assembly 50 (distal translation of the knife assembly 50 is not explicitly shown).

Trailing and leading stops 48*a* and 48*b* extend inwardly from an interior wall 47 of the portion 40*b* and may be positioned at predetermined positions therealong. The specific positions of the trailing and leading stops 48*a* and 48*b* on the interior wall 47 may depend on, for example, a contemplated retracted position of the knife assembly 50, a contemplated extended position of the knife blade assembly 50, etc. In the illustrated embodiment, leading stop 48*b* is positioned adjacent an aperture 49*b* (FIG. 5) that is aligned with a corresponding aperture 49*a* (FIG. 3) on the portion 40*a*. In one embodiment, apertures 49*a* and 49*b* of the blade stop 40 are configured to receive a pivot pin 34 therethrough so that the jaw members 22, 24 may pivot thereabout between the spaced-apart and approximated positions (see FIGS. 1 and 2).

Each of the portions 40*a* and 40*b* includes a respective elongated cam slot 68*a* and 68*b* that is configured to receive a cam pin 45 (FIGS. 1 and 2) therethrough such that the cam pin 45 may be translated therein when a drive tube (not shown in detail) that is connected to the cam pin 45 is actuated.

An optional groove 31 (FIG. 5) may be provided on one or both of the portions 40*a* and 40*b*. For illustrative purposes, the groove 31 is illustrated on the portions 40*a* and 40*b*. Groove 31 is configured to operably couple to one or more wires of the cable 20. Groove 31 facilitates maintaining the wire(s) in a relatively fixed position. As can be appreciated, this may reduce the likelihood of the wire(s) inadvertently contacting one or more components, e.g., knife assembly, of the forceps 2.

With reference again to FIGS. 1-2 end effector assembly 12 is designed as a bilateral assembly, i.e., where both jaw member 22 and jaw member 24 are moveable about pivot 34 relative to one another and to shaft 14. End effector assembly 12, however, may alternatively be configured as a unilateral assembly, i.e., where jaw member 24 is fixed relative to shaft 14 and jaw member 22 is moveable about pivot 34 relative to shaft 14 and fixed jaw member 24.

Knife blade channels 53 on the jaw members 22, 24 are aligned with the knife blade assembly 50 to accommodate reciprocation of a knife blade 52 therethrough when a trigger 11 of the trigger assembly 10 is moved proximally (FIGS. 1 and 2).

Knife blade assembly 50 is disposed within shaft 14 and is translatable therethrough from an initial retracted configuration to an extended configuration into the knife blade channels 53 on the jaw members 22, 24. Knife blade assembly 50 includes a generally elongated configuration having a split or bifurcated medial portion 55 defining opening 57 therebetween that is configured to receive the pivot pin 34 and cam pin 45 therethrough (FIG. 2). The opening 57 is configured to permit translation of the knife blade assembly through the blade stop 40. In addition, and as noted above, the proximal and distal ends 57*a* and 57*b*, respectively, of the opening are configured to contact the respective trailing and leading stops 48*a* and 48*b* to limit translation of the knife blade assembly 50.

In use, after tissue is electrosurgically treated, trigger 11 may be depressed or actuated to move knife blade assembly 50 distally to a deployed configuration to sever the electrosurgically treated tissue. Contact between proximal end 57*a* and the trailing stop 48*a* limits distal movement of the knife assembly 50. Releasing the trigger 11 moves the knife blade assembly 50 proximally back to a retracted configuration (FIG. 2). Contact between the distal end 57*b* and the leading stop 48*b* limits proximal movement of the knife assembly 50.

The unique configuration of the blade stop 40 overcomes the aforementioned drawbacks that are typically associated with conventional forceps that utilize one or more components associated therewith to limit proximal and/or distal movement of the knife blade assembly. That is, the likelihood of the knife blade assembly 50 developing "fatigue cracking" is reduced, if not eliminated, due to of the relatively soft plastic material of the blade stop 40.

From the foregoing and with reference to the various figure drawings, those skilled in the art will appreciate that certain modifications can also be made to the present disclosure without departing from the scope of the same. For example, in certain instances one or more resilient members, such as, for example, a spring or the like may be operably coupled to blade stop 40 to facilitate returning the knife blade assembly back to the retracted position.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
a housing having a shaft extending therefrom;
an end effector assembly operably coupled to a distal end of the shaft and including a pair of first and second jaw members, at least one of the first and second jaw members movable from an open configuration for positioning tissue therebetween, to a clamping configuration for grasping tissue therebetween;
a knife blade assembly including a knife blade translatable within the first and second jaw members when the first and second jaw members are in the clamping configuration, the knife blade assembly including a medial portion defining an opening therethrough having proximal and distal ends; and
a knife blade stop in operative communication with the knife blade assembly, the knife blade stop including a pair of leading and trailing stops thereon that are configured to contact respective distal and proximal ends of the opening to limit translation of the knife blade assembly.

2. An electrosurgical forceps according to claim 1, wherein the knife blade stop includes a leading opening and a trailing opening disposed therein and wherein the knife blade assembly is movable through the leading and trailing openings.

3. An electrosurgical forceps according to claim 1, wherein the knife blade stop includes an aperture that is configured to receive a pivot pin therethrough, the pivot pin providing a pivot for the first and second jaw members.

4. An electrosurgical forceps according to claim 1, wherein the knife blade stop includes an elongated slot that is configured to receive a cam pin therethrough, the cam pin configured to move the first and second jaw members between the open and clamping configurations.

5. An electrosurgical forceps according to claim 1, wherein the knife blade stop further includes an elongated groove thereon that is configured to receive at least one wire that is configured to provide electrosurgical energy to the first and second jaw members.

6. An electrosurgical forceps according to claim 1, wherein knife blade stop is made from two portions of relatively soft injection molded plastic joined together in a mechanical manner.

7. An electrosurgical forceps according to claim 1, wherein at least the trailing stop of the pair of leading and trailing stops is disposed proximally of the first and second jaw members.

8. An electrosurgical forceps according to claim 1, wherein the knife blade is translatably disposed within the knife blade stop.

9. An electrosurgical forceps, comprising:
a housing having a shaft extending therefrom;
an end effector assembly operably coupled to a distal end of the shaft and including a pair of first and second jaw members, at least one of the first and second jaw members movable from an open configuration for positioning tissue therebetween, to a clamping configuration for grasping tissue therebetween;
a knife blade assembly including a knife blade translatable within the first and second jaw members when the first and second jaw members are in the clamping configuration, the knife blade assembly including a bifurcated medial portion defining an opening therethrough having proximal and distal ends; and
a knife blade stop configured to receive the knife blade assembly therethrough, the knife blade stop including a pair of leading and trailing stops thereon that are positionable within the opening defined by the bifurcated medial portion, the leading and trailing stops configured to contact respective distal and proximal ends of the opening to limit translation of the knife blade assembly, wherein the knife blade stop includes an aperture that is configured to receive a pivot pin therethrough, the pivot pin providing a pivot for the first and second jaw members, wherein the knife blade stop includes an elongated slot that is configured to receive a cam pin therethrough, the cam pin configured to move the first and second jaw members between the open and clamping configurations, the knife blade stop including an elongated groove thereon that is configured to receive at least one wire that is configured to provide electrosurgical energy to the first and second jaw members.

10. An electrosurgical forceps according to claim 9, wherein the knife blade stop includes a leading opening and a trailing opening disposed therein, and wherein the knife blade assembly is movable through the leading and trailing openings.

11. An electrosurgical forceps according to claim 9, wherein the knife blade stop is made from two portions of relatively soft injection molded plastic joined together in a mechanical manner.

12. An electrosurgical forceps according to claim 9, wherein at least the trailing stop of the pair of leading and trailing stops is disposed proximally of the first and second jaw members.

13. An electrosurgical forceps according to claim 9, wherein the knife blade is translatably disposed within the knife blade stop.

14. An electrosurgical forceps according to claim 9, wherein the leading stop of the pair of leading and trailing stops is disposed distally of the aperture and the trailing stop of the pair of leading and trailing stops is disposed proximally of the elongated slot.

* * * * *